US009888763B2

(12) United States Patent
Doll et al.

(10) Patent No.: US 9,888,763 B2
(45) Date of Patent: Feb. 13, 2018

(54) POSITION DETECTION OF AN ORAL CARE IMPLEMENT

(71) Applicant: Braun GmbH, Kronberg (DE)

(72) Inventors: Alexander Franz Doll, Kronberg (DE); Alexandre Halbach, Liège (BE)

(73) Assignee: BRAUN GMBH, Kronberg (DE)

( * ) Notice: Subject to any disclaimer, the term of this patent is extended or adjusted under 35 U.S.C. 154(b) by 76 days.

(21) Appl. No.: 14/573,552

(22) Filed: Dec. 17, 2014

(65) Prior Publication Data

US 2015/0230593 A1 Aug. 20, 2015

Related U.S. Application Data

(60) Provisional application No. 61/920,477, filed on Dec. 24, 2013.

(51) Int. Cl.
A61B 5/05 (2006.01)
A46B 15/00 (2006.01)
G01N 27/02 (2006.01)

(52) U.S. Cl.
CPC ...... A46B 15/0006 (2013.01); A46B 15/0002 (2013.01); G01N 27/02 (2013.01)

(58) Field of Classification Search
CPC ...... A61B 5/0537; A61B 5/053; A61B 5/4872
USPC ...................................................... 600/547
See application file for complete search history.

(56) References Cited

U.S. PATENT DOCUMENTS

| 5,800,467 | A | * | 9/1998 | Park | A61N 1/36521 607/17 |
| 7,917,203 | B2 | | 3/2011 | Brown et al. | |
| 8,479,341 | B2 | | 7/2013 | Iwahori | |
| 2012/0251975 | A1 | * | 10/2012 | Iwahori | A61C 17/221 433/119 |
| 2012/0266397 | A1 | | 10/2012 | Iwahori | |
| 2012/0295216 | A1 | * | 11/2012 | Dykes | A61C 19/04 433/27 |
| 2013/0071807 | A1 | * | 3/2013 | Doll | A61N 1/32 433/27 |

(Continued)

FOREIGN PATENT DOCUMENTS

WO  WO02100268 A1  12/2002
WO  WO03104782 A1  12/2003

(Continued)

Primary Examiner — Daniel Cerioni

(57) ABSTRACT

An oral care implement (1) comprising: an electrode pair with an impedance formed therebetween when electrified; a frequency generator, electrically connected to the electrode pair, for applying a voltage with at least two different frequencies between the electrode pair; an impedance measurement unit, electrically coupled to the electrode pair, for measuring impedance values between the electrode pair at least at the different frequencies; and a contact determination unit, in communication with the impedance measurement unit, wherein the contact determination unit comprises a memory for storing a function, wherein the function correlates impedance values of a defined oral area at the different frequencies, and wherein the contact determination unit comprises a processor for processing the measured impedance values to the stored function so as to determine contact information of the electrode pair with the defined oral area.

11 Claims, 10 Drawing Sheets

(56) References Cited

U.S. PATENT DOCUMENTS

2013/0080295 A1* 3/2013 Dykes ................ A61C 17/221
 705/27.1
2013/0337401 A1* 12/2013 Aeby ................... A61C 19/041
 433/27

FOREIGN PATENT DOCUMENTS

WO  WO2008060482 A2  5/2008
WO  WO2011077282 A1  6/2011

* cited by examiner

POSITION DETECTION OF AN ORAL CARE IMPLEMENT

FIELD OF THE INVENTION

The present invention is directed to detecting oral cavity positions of an oral care implement during use.

BACKGROUND OF THE INVENTION

Maintaining good oral hygiene is important for oral health and even overall well-being. Proper and regular tooth brushing is a basic and important part of an oral care regimen. Various toothbrushes, including manual toothbrushes and electric toothbrushes, have been developed to facilitate effective tooth brushing. Researchers have continuously tried to improve the brushing quality, for example, by optimizing the brushing head, increasing the head rotation frequency, designing new cleaning techniques such as by way of ultrasound. Although some of these attempts have been successful in theory and even endorsed by dentists, high brushing quality has not been achieved in practice by many consumers. There are several explanations proposed. For example, at least one study reports that an adult brushes on average for 46 seconds while the recommended brushing time is generally accepted as 2 minutes. Studies even show that during this short brushing time consumers tend to brush unevenly, neglecting certain teeth surfaces and over-brushing others. This possibly leads to cavity formation and/or plaque accumulation in those surfaces where there is not enough brushing, and receding gums where there is too much brushing. Therefore, it is important for the consumer to receive real-time feedback on the brushing position and time, to optimize their brushing procedure. Such feedback relies on the ability to precisely and accurately detect the position of the toothbrush in the mouth.

There have been efforts in developing position detection technology for about a decade. However, to date no one has broadly and cost effectively commercialized this technology. There continues to be a need of providing non-intrusive, precise and/or accurate position detection at a low cost. Position detection technology will help users improve their brushing procedure so as to mitigate the occurrence of plaque and caries, as well as gum recession.

SUMMARY OF THE INVENTION

The present invention attempts to address one or more of these needs. In one aspect, the present invention provides an oral care implement, comprising:

an electrode pair with an impedance formed therebetween when electrified;

a frequency generator, electrically connected to the electrode pair, for applying a voltage with at least two different frequencies between the electrode pair;

an impedance measurement unit, electrically coupled to the electrode pair, for measuring impedance values between the electrode pair at least at the different frequencies; and a contact determination unit, in communication with the impedance measurement unit, wherein the contact determination unit comprises a memory for storing a function, wherein the function correlates impedance values of a defined oral area at the different frequencies, and wherein the contact determination unit comprises a processor for processing the measured impedance values to the stored function so as to determine contact information of the electrode pair with the defined oral area.

In another aspect, the present invention provides a method of detecting contact of a defined oral area by a side of an oral care implement, comprising the steps:

(a) providing an electrode pair on the side of the oral care implement;

(b) electrifying the provided electrode pair with a voltage to form an impedance between the electrode pair;

(c) applying at least two different frequencies to the voltage between the electrified electrode pair;

(d) measuring impedance values of the formed impedance between the electrified electrode pair at the applied different frequencies;

(e) defining a function that correlates impedance values of the defined oral area at the applied different frequencies; and (f) processing the measured impedance values to the defined function so as to detect whether the side of the oral care implement is contacting the defined oral area.

In a further aspect, the present invention provides a method of determining an oral cavity position of an oral care implement, comprising the steps:

(a) detecting contact information of the oral care implement by using the method according to aforementioned method wherein the contact information comprises whether a side of the oral care implement is contacting a defined oral area;

(b) detecting orientation information of the oral care implement; and (c) determining, based on at least the detected contact information and the detected orientation information, the oral cavity position of the oral care implement.

These and other features, aspects, and advantages of the present invention will become evident to those skilled in the art from the detailed description which follows.

BRIEF DESCRIPTION OF THE DRAWINGS

While the specification concludes with claims particularly defining and distinctly claiming the invention, it is believed that the invention will be better understood from the following description of the accompanying figures. In the accompanying figures.

DETAILED DESCRIPTION OF THE INVENTION

Figure 1A:
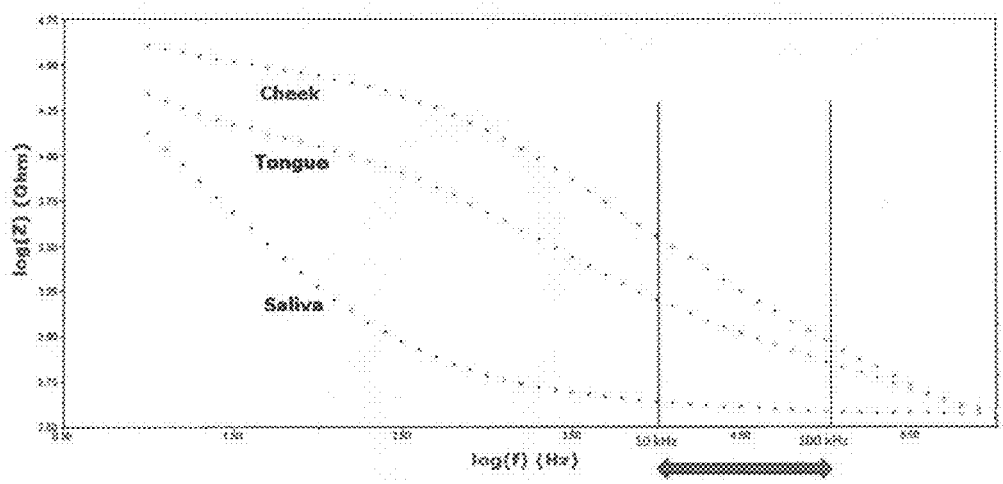
FIG. 1(a) shows an impedance magnitude variation of cheek area, tongue area, and saliva area over frequency.

As used herein, the articles including "a", "an", and "the" are understood to mean one or more of what is claimed or described.

As used herein, the terms "comprise", "comprises", "comprising", "include", "includes", "including", "contain", "contains", and "containing" are meant to be non-limiting, i.e., other steps and other sections which do not affect the end of result can be added. The above terms encompass the terms "consisting of" and "consisting essentially of".

According to the present invention, an oral care implement, which enables oral area contact detection and even oral cavity position detection, is provided. The present invention is based on the surprising discovery that certain oral areas of the oral cavity have unique impedance signatures when impedance is assessed and compared at different voltage frequencies. Furthermore, these impedance signatures (at different voltage frequencies) are even more pronounced between oral areas at certain frequency ranges. Without wishing to be bound by theory, it is the unique conductivity/dielectricity of each oral area that provides for the unique impendence signature at different voltage frequencies (at frequency ranges). This important discovery leads to more accuracy and/or precision in oral area contact detection and oral cavity position detection of an oral care implement.

The term "oral area", as used herein, refers to a distinct part or section inside an oral cavity, including but not limited to, cheek area, tongue area, saliva area, tooth area, gum area, hard palate area, soft palate area, and lip area. Specifically, the oral care implement comprises an electrode pair, a frequency generator, an impedance measurement unit and a contact determination unit. The electrode pair is preferably disposed on a side of the oral care implement that contacts various oral areas during the implement's use in the oral cavity. An impedance is formed between the electrode pair when electrified. Electricity can be provided by way of a battery (contained within the implement) or a pluggable wall socket. The frequency generator is electrically connected to the electrode pair, for applying a voltage with at least two different frequencies between the electrode pair. The change in frequencies happens preferably within about 1 s, 500 ms, 50 ms, 10 ms, 5 ms, or even 1 ms. The impedance measurement unit is electrically coupled to the electrode pair, for measuring impedance values between the electrode pair at the different frequencies. The term "impedance value" is used herein the broadest sense to include any value that can be derived from assessing conductivity/dielectricity between electrodes including but not limited to impedance magnitude, impedance phase, relative permittivity, and combinations thereof.

A "defined oral area" is a predetermined oral area of which the impedance value has been assessed and can be used as a reference. In the case that the electrode pair is contacting a defined oral area such as a saliva area, a cheek area or a tongue area, the impedance values may be quite different at different frequencies due to the oral area's specific conductivity/dielectricity. Therefore, the contact determination unit is used to determine contact information of the electrode pair based on this specific conductivity/dielectricity. The contact determination unit comprises a memory for storing a function. The function correlates impedance values of the defined oral area at the different frequencies, which reflects the specific conductivity/dielectricity of the defined oral area. In turn, the contact determination unit is in communication with the impedance measurement unit. As used herein, the term "in communication with" means there is data transmission between two elements connected by this term. The communication method may be of any form, including wireless communication or hard-wired communication. Some examples of the communication methods are discussed in, for example, US20130311278A at paragraphs 39 to 41.

The contact determination unit comprises a processor for processing the measured impedance values to the stored function(s) so as to determine contact information of the electrode pair with the defined oral area(s). Specifically, if a particular measured impedance value meets the specific conductivity/dielectricity represented by a stored function, it will be determined that the electrode pair is contacting the defined oral area (to which the stored function corresponds). If the measured impedance value does not meet the specific conductivity/dielectricity represented by the stored function, it will be determined that the electrode pair is not contacting the defined oral area (to which the stored function corresponds). The oral care implement may further comprise a position determination unit, which is in communication with the contact determination unit. The position determination unit is configured for determining an oral cavity position of the implement based on at least the determined contact information.

Without wishing to be bound by theory, the present invention improves the accuracy and/or precision of position detection by, in part, the use of a frequency generator to generate at least two different voltage frequencies, and measuring at different frequencies. Indeed, it is surprisingly found that different oral areas have different impedance signatures (e.g., between two frequencies). Furthermore, this difference is even more pronounced within certain frequency ranges. Impedance value measurements at different frequencies allow differentiation among different oral tissues within the oral cavity (e.g., tongue and cheek) and saliva. This is in contrast to single frequency devices or those devices that do not measure at different frequencies which merely can determine if "contact" is made.

Among various oral areas, the saliva area basically consists of water and/or a toothpaste slurry and therefore has a lot of ions which may contribute to its conductivity. The oral areas comprising oral tissues, such as the cheek area and the tongue area also have conductivity because of the huge amount of water they contain. However, oral tissues further comprise cells in addition to the water. This will contribute to the dielectricity of the oral tissues and cause a visible difference in the impedance versus frequency diagram of saliva and oral tissues. The main characteristics in the variation of oral tissue impedance over the frequency can be grouped in three categories: α dispersion, β dispersion, and γ dispersion. The α dispersion contributes to the impedance change of any conductor at low frequencies in the hertz range. The β dispersion is found in living tissue in the kilohertz to megahertz range, and is caused by the cellular membranes. The γ dispersion is a high frequency phenomenon in the gigahertz range due to the polarization of water molecules. Therefore, these different oral area may show different conductivity/dielectricity due to their different composition. For example, the amount of water and/or cells contained in the oral area, the shape of the cells, the arrangement of the cells may all cause the conductivity/dielectricity of a certain oral area to differ from other oral areas.

FIG. 1(a) is a graph showing a typical impedance magnitude variation at different frequencies for the cheek area, the tongue area, and the saliva area. The graph demonstrates that these oral areas can be differentiated between each other based on their impedance values (at different voltage frequencies). The x axis of the FIG. 1(a) graph represents frequency in hertz (Hz) on a log scale from 0.50 to 6.00. The y axis of the FIG. 1(a) graph represents impedance magnitude in ohm ($\Omega$) on a log scale from 2.50 to 4.75. It can be seen that the cheek area, the tongue area and the saliva area have quite different impedance magnitudes at various frequencies. For example, the impedance magnitude of the saliva area drops sharply between the frequencies from 10 Hz to 1 kHz, and then stabilizes over a broad range up to almost 1 MHz. For the cheek area and the tongue area, the sharp drop of the impedance magnitude appears in the range from 1 kHz to 1 MHz, with different drop rates. Therefore, in an embodiment, the function correlating impedance values of the defined oral area at the different frequencies may be a linear function reflecting the drop rate at a certain frequency range. For example, it can be seen that the drop rate of the impedance magnitude at a frequency range from 10 kHz to 100 kHz is quite different among the cheek area, the tongue area, and the saliva area. In an alternative embodiment, the function correlating impedance values of the defined oral area at the different frequencies may be selected from the group consisting of a quadratic function, a cubic function, a quartic function, a quintic function, a sextic function, and a rational function, provided that the selected function can be used to differentiate the defined oral area from other oral areas at a certain frequency range.

Figure 1B:
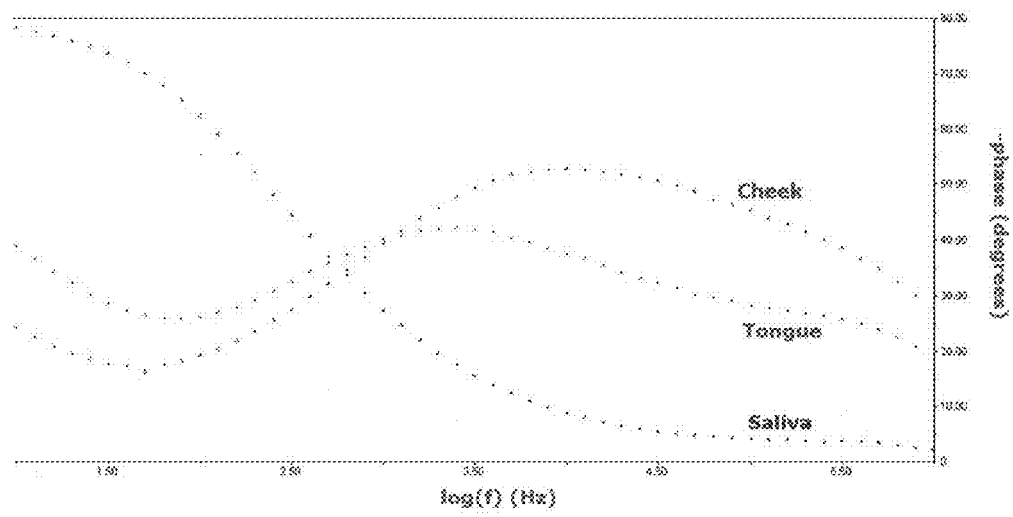
FIG. 1(b) shows an impedance phase angle variation of cheek area, tongue area, and saliva area over frequency.

FIG. 1(b) is a graph showing a typical impedance phase angle variation at different frequencies for the cheek area, the tongue area, and the saliva area. The x axis of the FIG. 1(b) graph represents frequency in hertz (Hz) on a log scale from 1.00 to 6.00. The y axis of the FIG. 1(b) graph represents impedance phase angle in degree (°) from 0° to 80°. It can be seen that the cheek area, the tongue area and the saliva area have quite different impedance phase angle at various frequencies. For example, the impedance phase angle of the saliva area drops sharply from 100 Hz to 10 kHz, and then stabilizes over a broad range up to almost 1 MHz. The impedance phase angle of the cheek area decreases sharply at low frequencies form 10 Hz to 50 Hz, and then increases sharply from 50 Hz to almost 10 kHz, and then decreases again at high frequencies up to 1 MHz. The impedance phase of the tongue area decreases sharply at low frequencies form 10 Hz to 100 Hz, and then increases sharply from 100 Hz to 1 kHz, and then decreases again at high frequencies up to 1 MHz. In one embodiment, a certain frequency range, for example, 100 Hz to 1 kHz, can be selected to differentiate the cheek area, the tongue area, and the saliva area by the drop rate of the impedance phase angle.

The oral care implement of the present invention may take the form of a toothbrush, a flosser, an oral irrigator, a tongue scraper, an interdental cleaner, an oral appliance and any other oral or dental devices which, at least a part of which, need to be utilized in the oral cavity. However, for the sake of convenience, the following description focuses primarily on toothbrushes to further explain the present invention. These descriptions are given solely for the purpose of illustration and are not meant to be construed as limitations of the present invention, as many variations of the embodiments described hereinafter are possible without departing from the spirit and scope of the present invention.

Configuration

Figures 2A, 2B:
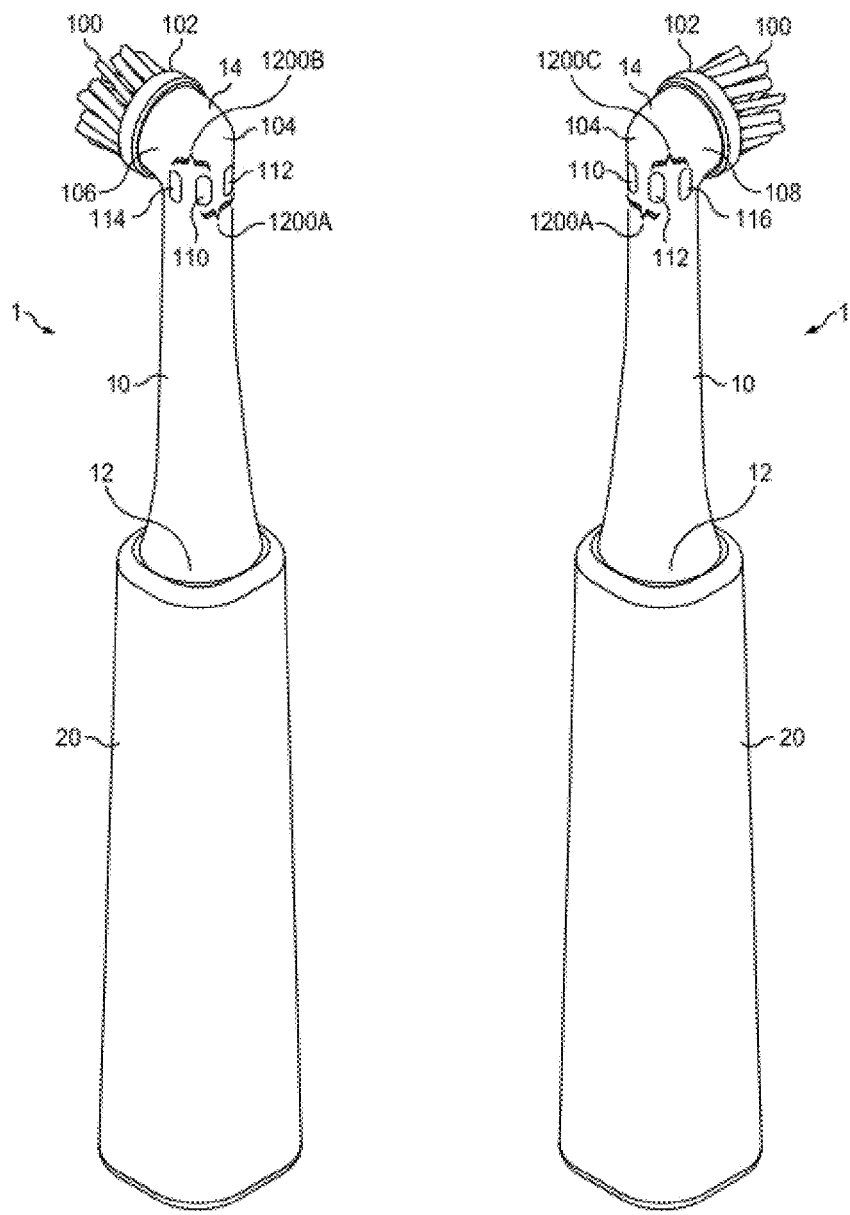
FIG. 2(a) is a left perspective view of a toothbrush according to an embodiment of the present invention.
FIG. 2(b) is a right perspective view of a toothbrush according to the embodiment of FIG. 2(a)

FIGS. 2(a) and 2(b) illustrate a toothbrush 1 as embodiment of the invention, wherein the toothbrush 1 comprising a brushhead portion 10 and a handle portion 20. FIG. 2(a) shows a left perspective view of the toothbrush 1 while FIG. 2(b) shows a right perspective view of the toothbrush 1. The brushhead portion 10 has a first end 12 and an opposing second end 14. The brushhead portion 10 is connected to a handle portion 20 at its first end 12. The brushhead portion 10 comprises a bristle side 102 with bristles 100 suitable for brushing teeth. The bristles 100 are disposed closer to the second end 14 than to the first end 12. A rear side 104 opposes the bristle side 102. The brushhead portion 10 further comprises a first side 106, and a second side 108 opposing the first side 106. The first side 106 and the second side 108 each separate the bristle side 102 and the rear side 104. The first side 106, the rear side 104, the second side 108, and the bristle side 102 circumferentially define the brushhead portion 10. During use, at least a part of the brushhead portion 10 is put into the oral cavity of a user and the bristles 100 make contact with the user's teeth or gum. The handle portion 20 is gripped by the user. The handle portion 20 may contain a battery therein (not shown) to provide electricity to the various electrical components (e.g., the frequency generator and other electrical components which will be discussed later on) of the device. The battery may be disposable or rechargeable.

Referring to FIGS. 2(a) and 2(b), a first electrode 110 and a second electrode 112 are disposed on the rear side 104 and form a first electrode pair 1200A. A third electrode 114 is disposed on the first side 106 and in closer proximity to the first electrode 110 than to the second electrode 112. A fourth electrode 116 is disposed on the second side 108 and in closer proximity to the second electrode 112 than to the first electrode 110. The first electrode 110 and the third electrode 114 form a second electrode pair 1200B. The second electrode 112 and the fourth electrode 116 form a third electrode pair 1200C. In a further embodiment, a fifth electrode (not shown) may be disposed on the rear side 104 to form a fourth electrode pair (not shown) with either the first electrode 110 or the second electrode 112, and even form a fifth electrode pair (not shown) with either the second electrode 112 or the first electrode 110. Such an arrangement is especially advantageous when not all contact of the rear side 104 with a defined oral area can be detected by the first electrode pair 1200A. For example, in some cases, only one electrode (either the first electrode 110 or the second electrode 112) is contacting a defined oral area and therefore the contact will be not detected by this first electrode pair 1200A. The fourth and even fifth electrode pair will help to cover the relatively large surface area of the rear side 104 and therefore make sure any contact of the rear side 104 with a defined oral area will be able to be detected. In a further embodiment, additional electrode pairs may be disposed around the brushhead portion 10 as needed to enable even more precise contact information with a defined oral area (depending upon factors that may include cost constraints, extent of the surface area, and precision needed). Each of the electrodes may employ a conductive resin or metal material, and may be formed integrally with the brushhead portion 10, or may be assembled/connected to the brushhead portion 10.

Each of the electrode pairs 1200A, 1200B and 1200C is in electrical communication within an electrical circuit, and impedance may be formed between each of the electrode pair 1200A, 1200B, and 1200C when electrified.

Figure 3:
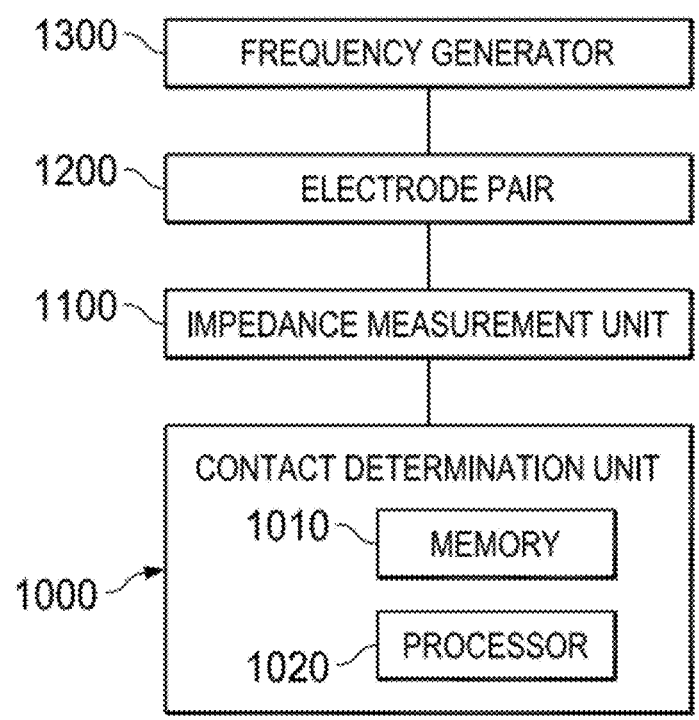
FIG. 3 is a block diagram illustrating an electrical circuit for determining contact information of an electrode pair according to an embodiment of the present invention.

FIG. 3 shows a block diagram illustrating the electrical circuit for determining contact information of the electrode pair with a defined oral area according to an embodiment of the present invention. In FIG. 3, an electrode pair 1200 is used to refer to any one of the first electrode pair 1200A, the second electrode pair 1200B, and the third electrode pair 1200C as shown in FIGS. 2(*a*) and 2(*b*). Referring to FIG. 3, a frequency generator 1300 is electrically connected to the electrode pair 1200, for applying a voltage with at least two different frequencies between the electrode pair 1200. The electrical connection between the frequency generator 1300 and the electrode pair 1200 may be achieved by a wire connection, for example, via a flexible copper wire or cable. The frequency generator 1300 is preferably operable to generate frequencies ranging from 1 kHz, 10 kHz, or 50 kHz to 100 kHz, 500 kHz, or 1 MHz, although other frequency ranges are also possible. In an embodiment, the frequency generator 1300 may alternately generate and alternate between two frequencies. Alternatively, the frequency generator 1300 may generate and alternate among 3, 4, 5, 6, 7, 8, 9, 10 or more frequencies. Yet alternatively still, the frequency generator 1300 may generate a non-stationary frequency spectrum, for example, in a waveform selected from sine waveform, square waveform, triangle waveform, sawtooth waveform, and combinations thereof. The selection of the frequency value and waveform may depend on the specific conductivity/dielectricity of the defined oral area. For example, a frequency range may be selected if the impedance of the defined oral area changes with a tendency to be significantly different from other oral areas when the frequency changes in this frequency range, so as to easily differentiate the defined oral area from the other oral areas. The frequency generator 1300 may be implemented by those manufactured by Harris Corporation (Melbourne, Fla.) or Hewlett Packard Corporation (Palo Alto, Calif.).

An impedance measurement unit 1100 is electrically coupled to the electrode pair 1200, for measuring impedance values between the electrode pair at different frequencies. In an embodiment, the impedance measurement unit 1100 may be physically connected to the electrode pair 1200 by a wire connection, for example, via a flexible copper wire or cable. In another embodiment, the impedance measurement unit 1100 may be wirelessly coupled to the electrode pair 1200, for example, using laser and piezoelectric transducers (see, e.g., Hyun-Jun Park, Hoon Sohn, Chung-Bang Yun, Joseph Chung and Il-Bum Kwon. A wireless guided wave excitation technique based on laser and optoelectronics. *Smart Structures and Systems*, Vol 6, No. 5-6, 2010, 749-765). The impedance measurement unit 1100 may follow a measurement method selected from the group consisting of bridge method (such as Wheatstone Bridge method), resonant method, I-V (current-voltage) method, RF (radio frequency) I-V method, network analysis method, auto balancing bridge method, and combinations thereof. The choice of the impedance measurement method may depend on some factors such as the frequency range, measurement range, measurement accuracy and ease of operation. For example, the auto balancing bridge method may ensure a high accuracy measurement for a broad frequency range from 1 MHz to 110 MHz, the RF I-V method may have the best measurement capability for frequency range from 100 MHz to 3 GHz, and the network analysis may be the recommended technique when the frequency ranges from 3 GHz and up. The impedance measurement unit 1100 may be implemented by those manufactured by Agilent Technologies (Santa Clara, Calif.).

A contact determination unit 1000 is in communication with the impedance measurement unit 1100, for determining contact information. When the electrode pair 1200 is electrified and contacting a defined oral area, a closed circuit is formed with an electrical current going through the defined oral area. The impedance of the defined oral area is measured as a reaction to the electrical current and represents the conductivity/dielectricity of the defined oral area. Different oral areas may have different conductivity/dielectricity measurement due to different compositions and structures. For example, the more water a particular oral area contains, the more conductive it is, and therefore the more constant its impedance is over a broad frequency range (as compared to those areas having less water). The present invention is based on the different conductivity/dielectricity of various oral areas at different electrical frequencies. Therefore, the contact determination unit 1000 may comprise a memory 1010 for storing a function, wherein the function correlates impedance values of a defined oral area at different frequencies. The function may relate to one or more oral areas selected from the group consisting of cheek area, tongue area, and saliva area as discussed hereinabove with respect to FIGS. 1(*a*) and 1(*b*). The contact determination unit 1000 may further comprise a processor 1020 for processing the measured impedance values to the stored function so as to determine contact information of the electrode pair 1200 with the defined oral area. The memory 1010 and the processor 1020 may each independently be embodied in any form and may be associated with each other in any form. Some examples of the memory 1010 and the processor 1020, as well as their association, may be found in, for example, US20130176750A1 at paragraphs 426 to 431.

Figure 4A:
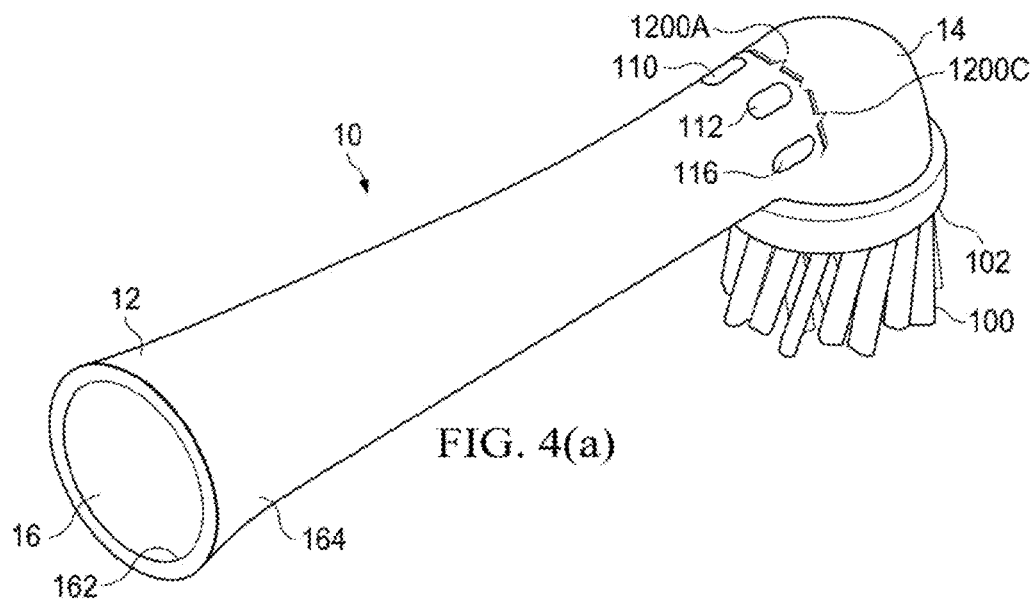
FIG. 4(a) is a perspective view of the brushhead portion of the toothbrush according to the embodiment of FIG. 2(a)
Figure 4B:
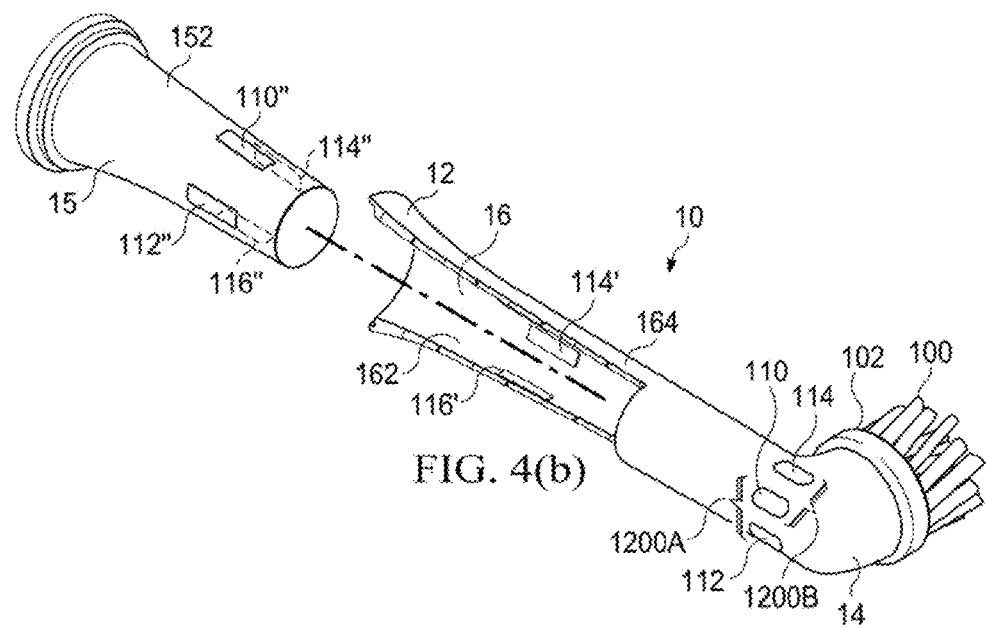
FIG. 4(b) is a partially sectional view of the brushhead portion of the toothbrush according to the embodiment of FIG. 2(a), showing how the brushhead portion is connected with a connector.
Figure 4C:
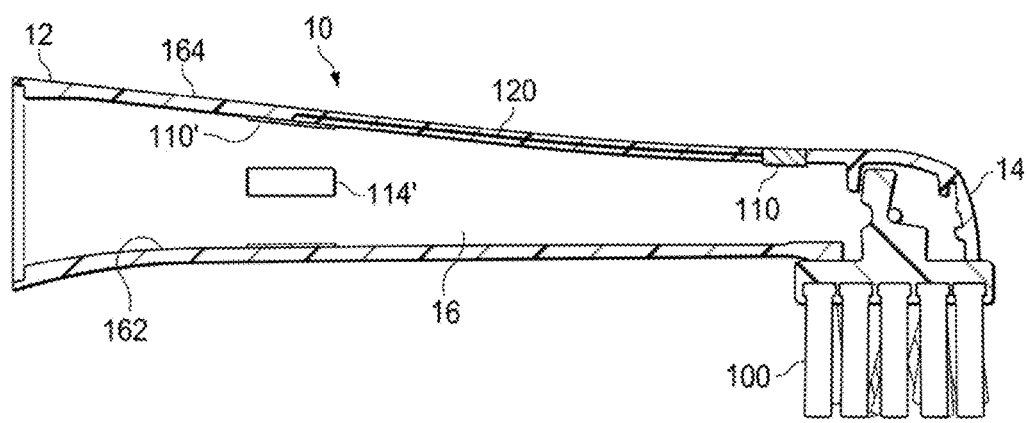
FIG. 4(c) is a sectional view of the brushhead portion of the toothbrush according to the embodiment of FIG. 2(a), with the cut plane orthogonal to the bristle side of the brushhead portion and going through the first electrode.

The frequency generator 1300, the impedance measurement unit 1100 and the contact determination unit 1000 may be integrated into a printed circuit board (PCB, not shown). The PCB may be accommodated in the brushhead portion 10 or in the handle portion 20 as shown in FIGS. 2(*a*) and 2(*b*). In an embodiment, the PCB is accommodated in the handle portion 20. In this case, referring to FIGS. 4(*a*) to 4(*c*), the electrodes 110, 112, 114 and 116 may be connected to the PCB via a connector 15 connecting the brushhead portion 10 and the handle portion 20. The brushhead portion 10 may comprise an essentially cylindrical hollow tube 16 to receive the connector 15. The hollow tube 16 may have an inner wall 162 and an outer wall 164. The connector 15 may have an outer surface 152 which is fittable into at least a part of the hollow tube 16 and lockable with the hollow tube 16. The electrical connection between the brushhead portion 10 and the connector 15 is achieved by conductors 110', 112'(not shown), 114', 116', 110", 112", 114", and 116" disposed on the inner wall 162 of the hollow tube 16 and the outer surface 152 of the connector 15. The number of the conductors disposed on the inner wall 162 of the hollow tube 16 should be equivalent to the number of the electrodes. Each of the electrodes may be connected to its respective conductor on the inner wall 162 of the hollow tube 16 via a line. For example, as shown in FIG. 4(*c*), the first electrode 110 is connected to a conductor 110' via a line 120. The line 120 may be buried between the inner wall 162 and the outer wall 164 of the hollow tube 16. Alternatively, the line may be attached to the inner wall of the hollow tube. The first electrode 110, the line 120 and the conductor 110' may be formed integrally or may be assembled/connected together.

The connector 15 may be electrically connected to the handle portion 20 in a similar way.

Figure 5:
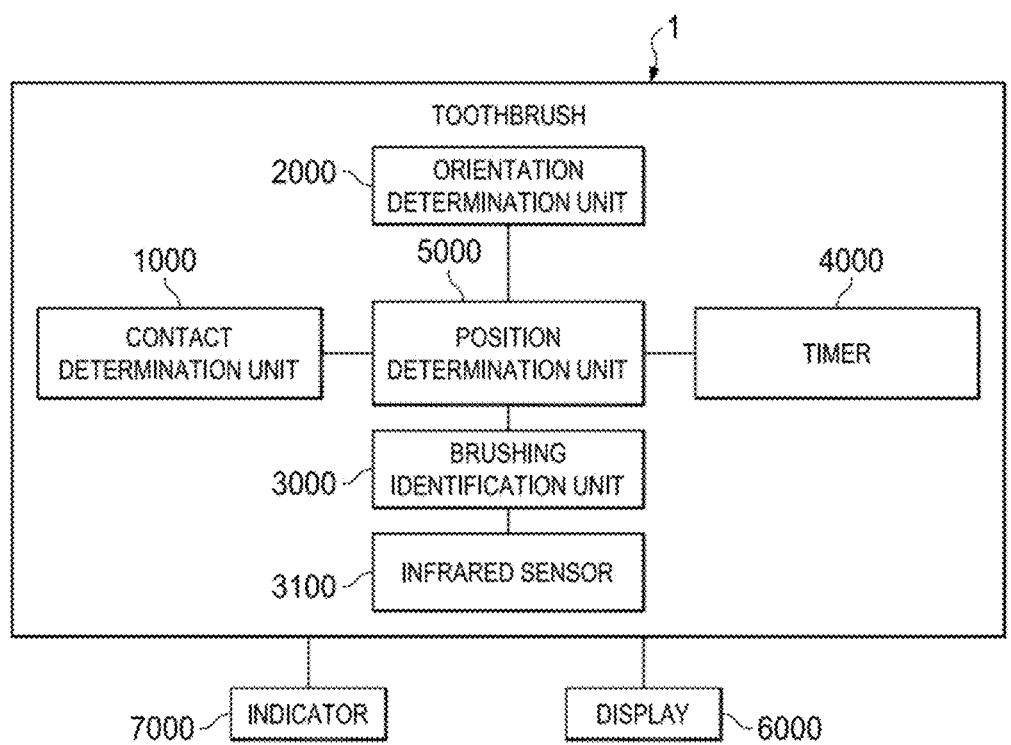
FIG. 5 is a block diagram illustrating a toothbrush comprising the electrical circuit for determining contact information according to the embodiment of FIG. 3.

FIG. 5 shows a block diagram illustrating a toothbrush comprising the electrical circuit for determining contact information according to a specific embodiment. Referring to FIG. 5, the toothbrush 1 further comprises a position determination unit 5000. The position determination unit 5000 may be in communication with the contact determination unit 1000, for determining an oral cavity position of the toothbrush 1 based on at least the determined contact information. As used herein, the term "contact information" relates to whether a given side (e.g., the bristle side 102, the rear side 104, the first side 106, and the second side 108 as shown in FIGS. 2(a) and 2(b)) of the brushhead portion, on which an electrode pair is disposed, is contacting a defined oral area. Based on this information, an oral cavity position may be estimated (in a given point of time). For example, referring back to FIGS. 2(a) and 2(b), if the rear side 104 is contacting the cheek during brushing, it can be estimated that the oral cavity position of the brushhead portion 10 is between the cheek and the teeth with the bristle side 102 facing the teeth.

Referring to FIG. 5, in order to detect the oral cavity position (i.e., providing more location details than contact information), the toothbrush may further comprise an orientation determination unit 2000 in communication with the position determination unit 5000. The orientation determination unit 2000 may be configured for obtaining orientation information of the toothbrush 1, and the position determination unit 5000 may be configured for determining the oral cavity position further based on the obtained orientation information. The orientation determination unit 2000 may be selected from the group consisting of a 3-axis accelerometer, a 3-axis gyroscope, a geomagnetic sensor, and combinations thereof. In an embodiment, referring to FIG. 6, a 3-axis (x, y, and z axes) accelerometer (not shown) is provided within the handle portion 20, for example, attached to the PCB (not shown) inside the handle portion 20. The accelerometer may be installed so that the x axis is parallel to the bristle side 102 and orthogonal to a lengthwise elongation axis L of the toothbrush 1, the y axis matches the lengthwise elongation axis L of the toothbrush 1, and the z axis is orthogonal to the bristle side 102. A gravity acceleration vector may be used to indicate the orientation of the toothbrush 1. For example, when the toothbrush 1 vertically stands on a horizontal table surface with the lengthwise elongation axis L of the toothbrush 1 orthogonal to the horizontal table surface, the gravity acceleration vector is parallel to the y axis. When the toothbrush 1 is placed horizontally with the lengthwise elongation axis L of the toothbrush 1 parallel to a horizontal plane, and with the bristle side 102 of the brushhead portion 10 pointing upward, the gravity acceleration vector is parallel to the z axis. When toothbrush 1 is placed horizontally with the lengthwise elongation axis L of the toothbrush 1 parallel to a horizontal plane, and with the bristle side 102 is pointed sideways, the gravity acceleration vector is parallel to the x axis.

In an embodiment, the 3-axis accelerometer comprises a micro electro mechanical system (MEMS). In a further embodiment, the accelerometer comprises a MEMS sensor selected from the group consisting of a piezoelectric resistance-type MEMS, an electrostatic capacitance-type MEMS, a thermal detection-type MEMS, and the combinations thereof. MEMS sensors are extremely small and can therefore easily be incorporated into the toothbrush. Although not particularly shown, it is beneficial to provide correction circuits for correcting the balance of sensitivities, temperature characteristics of the sensitivities, temperature drift, and so on of the accelerometer in the respective axes. Furthermore, a band pass filter (low-pass filter) for removing dynamic acceleration components, noise, and so on may be provided. Further still, noise may be reduced by smoothing the waveforms of the outputs from the accelerometer.

Referring back to FIG. 5, the toothbrush 1 may further comprise an infrared sensor 3100 for sensing a temperature of bristles, and a brushing identification unit 3000, in communication with the infrared sensor 3100, for identifying contact information of the bristles with tooth or gum based on the sensed bristle temperature. The infrared sensor 3100 may be able to sense each bristle's temperature. Alternatively, the infrared sensor 3100 may be disposed on the bristle side 102 of the brushhead portion 10 as shown in FIGS. 2(a) and 2(b) to sense a temperature of an object facing the bristle side 102. The object facing the bristle side 102 during toothbrushing may be tooth or gum. The brushing identification unit 3000 may be configured for identifying whether the bristle side 102 is facing tooth or gum based on the sensed temperature. The position determination unit 5000 may be in communication with the brushing identification unit 3000, and configured for determining the oral cavity position further based on the identified contact information of the bristles with tooth or gum. The infrared sensor 3100 may be disposed on the bristle side of the brushhead portion, or even on the bristles, or any other location where the bristle temperature sensing can be actuated. The infrared sensor 3100 may be, but is not limited to, a thermocouple or a thermopile.

The toothbrush 1 may further comprise a timer 4000. The timer 4000 may be configured for measuring a time duration at an oral cavity position. A display 6000 may be provided in communication with the toothbrush 1. The display 6000 may be configured for displaying the time duration at each oral cavity position. The display 6000 may be integrated into the toothbrush 1 or physically separate from the toothbrush 1. An indicator 7000 may also be provided in data communication with the toothbrush 1. The indicator 7000 may be configured for indicating whether the time duration is shorter or longer than a predetermined amount of time. The indicator 7000 may be integrated into the toothbrush 1 or physically separate from the toothbrush 1, or even as a part of the display 6000.

Contact Information Determination

During a tooth brushing cycle, the oral areas that may be contacted by a side of a toothbrush head mainly include a cheek area, a tongue area, and a saliva area, while bristles disposed on the toothbrush head are contacting tooth and/or gum.

Referring back to FIGS. 2(a) and 2(b), four electrodes 110, 112, 114, and 116 are provided on the first side 106, the rear side 104 and the second side 108 of the brushhead portion 10 of the toothbrush 1. These four electrodes 110, 112, 114, and 116 constitute three electrode pairs 1200A, 1200B, and 1200C which can be used to determine whether each of the first side 106, the rear side 104 and the second side 108 is contacting a defined oral area or not. The defined oral area may be selected from the group consisting of cheek area, tongue area, saliva area, and combinations thereof.

During operation, each of the electrode pairs 1200A, 1200B, and 1200C (hereinafter collectively called as "the electrode pair 1200") is electrified with a voltage to form an impedance therebetween. The voltage may be preferably provided by an AC (alternating current) power source (e.g., a pluggable wall socket). Referring back to FIG. 3, at least two different frequencies are then applied by the frequency generator 1300 to the voltage between the electrified electrode pair 1200. Impedance values of the formed impedance between the electrified electrode pair 1200 are measured at the applied different frequencies by the impedance measurement unit 1100. The measurement of each electrode pair 1200A, 1200B, and 1200C may be simultaneous or in sequence. A function is defined such that it correlates impedance values of the defined oral area at the applied different frequencies, and stored in the memory 1010 of the contact determination unit 1000. The measured impedance values are then processed to the stored function in the processor 1020 of the contact determination unit 1000. If the measured impedance values meet the stored function, a contact with the defined oral area will be determined.

The following discussion is based on the impedance magnitude variation of the cheek area, the tongue area, and the saliva area to further explain the contact information determination. As discussed hereinabove with regard to FIG. 1(a), the drop rate of the impedance magnitude in a frequency range from 10 kHz to 100 kHz is quite different between the cheek area, the tongue area, and the saliva area. What's even more advantageous is that the impedance magnitude of all these three areas drops almost linearly when the frequency increases in the range from 10 kHz to 100 kHz. This makes it possible to use a very simple linear function to differentiate these three oral areas from each other, which requires the impedance magnitudes at only two different frequencies, and therefore consumes very low computation power. However, the skilled person in the art can readily understand that other frequency ranges and other functions reflecting the impedance magnitude variation over three or more frequencies may also be used alternatively to achieve the present invention. The skilled person in the art can also readily understand that other impedance values such as impedance phase as shown in FIG. 1(b) may also be used alternatively or even additionally to determine contact information.

Referring to FIG. 1(a), the linear function, which can be used to differentiate the cheek area, the tongue area and the saliva area in the frequency range from 10 kHz to 100 kHz, may comprise a ratio of A1/A2, wherein A1 is a first impedance magnitude measured at a first frequency, and A2 is a second impedance magnitude measured at a second frequency. Two threshold constants can be used to set limitations for identifying the cheek area, the tongue area, and the saliva area. For example, in the case when the second frequency is greater than the first frequency, when A1/A2 is less than a first threshold constant a, it can be identified as the saliva area. When A1/A2 is no less than a second threshold constant b, it can be identified as the cheek area. When A1/A2 is less than the second threshold constant b but no less than the first threshold constant a, it can be identified as the tongue area.

The value of the threshold constants may be determined by experimentation. For example, the first threshold constant a may be from 1.2 to 1.4, since this value generally cannot be reached by a contact with the saliva area while a contact with the tongue area can easily exceed this value. The second threshold constant b may be from 1.7 to 2.1 in differentiating a contact with the tongue area and a contact with the saliva area.

One or more functions may be defined and stored in the memory 1010. Each of the one or more functions correlates impedance values of one defined oral area at the applied different frequencies. The processor 1020 may process the measured impedance values to each of the one or more functions one-by-one to find the function which the measured impedance values meet (if at all).

Figure 7:
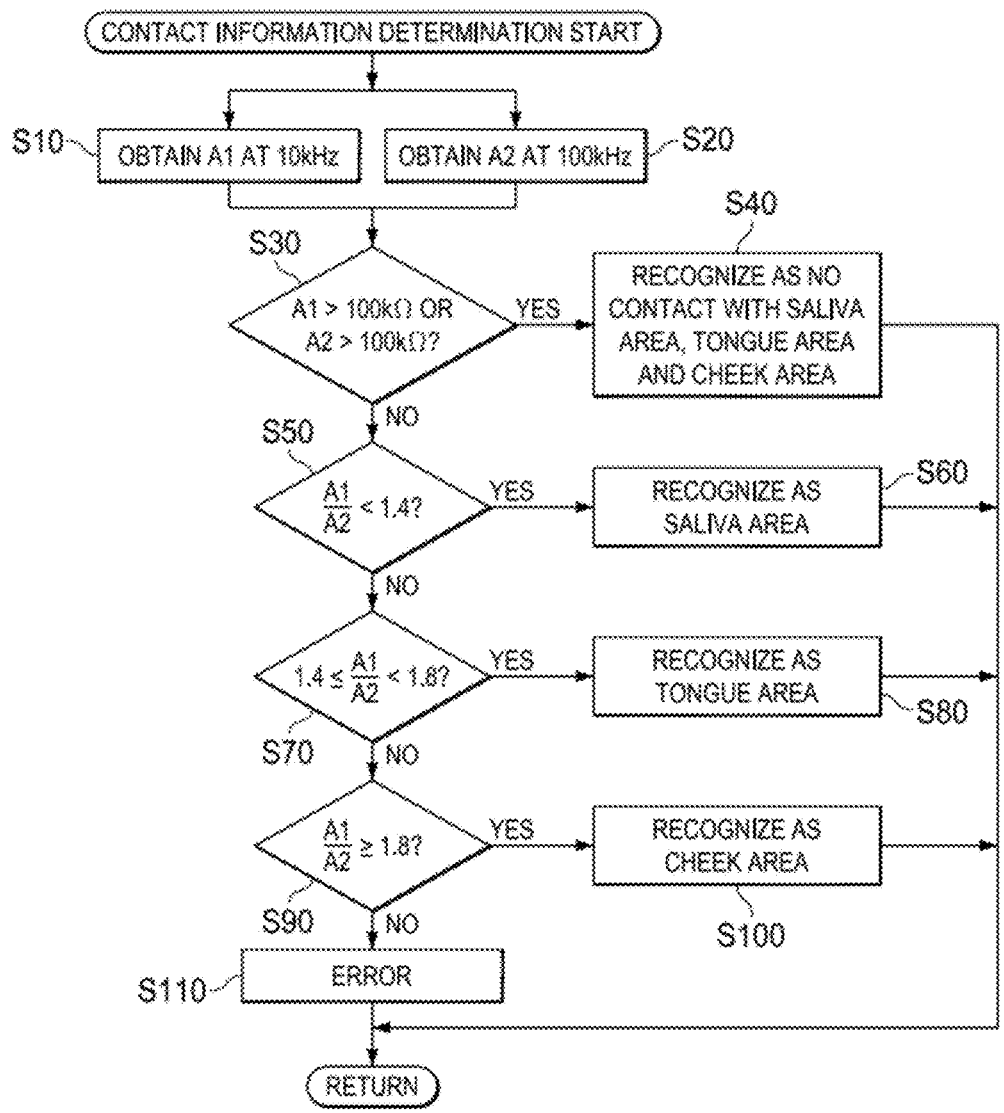
FIG. 7 shows a contact information determination process involving saliva area, tongue area and cheek area according to an embodiment of the present invention.

FIG. 7 shows an exemplary contact determination process to determine whether a side of the brushhead portion of the toothbrush is contacting the oral area selected from the saliva area, the tongue area, and the cheek area. The side has an electrode pair with a voltage to form an impedance therebetween. The applied different frequencies to the electrode pair comprise a first frequency (for example, 10 kHz) and a second frequency (for example, 100 kHz). A2 is a first impedance value (for example impedance magnitude) measured between the electrode pair at the first frequency (S10). A2 is a second impedance value (for example impedance magnitude) measured at the second frequency (S20) between the electrode pair. If any one of A1 and A2 is less than an impedance magnitude threshold (for example, 100 kΩ) ("YES" in S30), the side is recognized as not having contact with the saliva area, the tongue area or the cheek area (S40). The impedance magnitude threshold may be a value equal to or greater than the biggest impedance magnitude obtainable for the saliva area, the tongue area or the cheek area at the first and second frequencies. If neither A1 nor A2 is higher than the impedance magnitude threshold 100 kΩ ("NO" in S30), the side is contacting the saliva area, tongue area, or cheek area and therefore the process proceeds to S50. If the ratio of A1/A2 is less than 1.4 (YES in S50), the side is contacting with saliva area (S60). If the answer to S50 is "NO," the process proceeds to S70. If the ratio of A1/A2 is equal to or greater than 1.4 but less than 1.8 (YES in S70), the side is contacting the tongue area (S80). If the answer to S70 is NO, the process proceeds to S90. If the ratio of A1/A2 is equal to or greater than 1.8 (YES in S90), the side is contacting the cheek area (S100). If the answer to S90 is NO, an error message is returned (S110). The error may be due to either of A1 and A2 or both equal to 0, which indicates there may be a short circuit or other dysfunctions. Note that rather than providing an error message as in S110, the processes of S10 to S90 may instead be repeated until contact information (including no contact and a contact with the saliva area, the tongue area, or the cheek area) is recognized. Note also that all the values shown in this exemplary contact determination process, including the frequency value, the impedance magnitude threshold value, and the ratio value, may be adjusted or changed to fit specific user(s).

The whole contact determination process may happen within 1 s, 500 ms, 50 ms, 10 ms, or 5 ms. The whole contact determination process may be automatically repeated every 1 s, 2 s, 3 s, 5 s, or 8 s during the teeth brushing action. The impedance values at the applied different frequencies are preferably measured within a time interval of less than 500 ms, 300 ms, 100 ms, 50 ms, 10 ms, 5 ms, or even 1 ms. This helps to guarantee that the variation in the impedance values is due to the frequency change instead of a brush movement.

In practice, once the brushhead portion of a toothbrush is put into the oral cavity and the user begins to brush, a saliva layer will surround the brushhead portion. When the brushhead portion is contacting the cheek or the tongue, a contact pressure is formed to make the saliva layer become very thin. This very thin saliva layer will significantly affect the impedance between the electrode pair in a direct current (DC) circuit so that the contact with the cheek or the tongue cannot be detected. However, in an alternating current circuit having voltage at varying frequencies, by selecting an appropriate frequency range in which the impedance of the cheek and/or the tongue changes much more significantly than that of the saliva, this very thin saliva layer can be ignored in detection of a contact with the cheek or the tongue. The present invention advantageously makes use of this finding, and provides an accurate contact information determination.

Oral Cavity Position Determination

Figure 8:
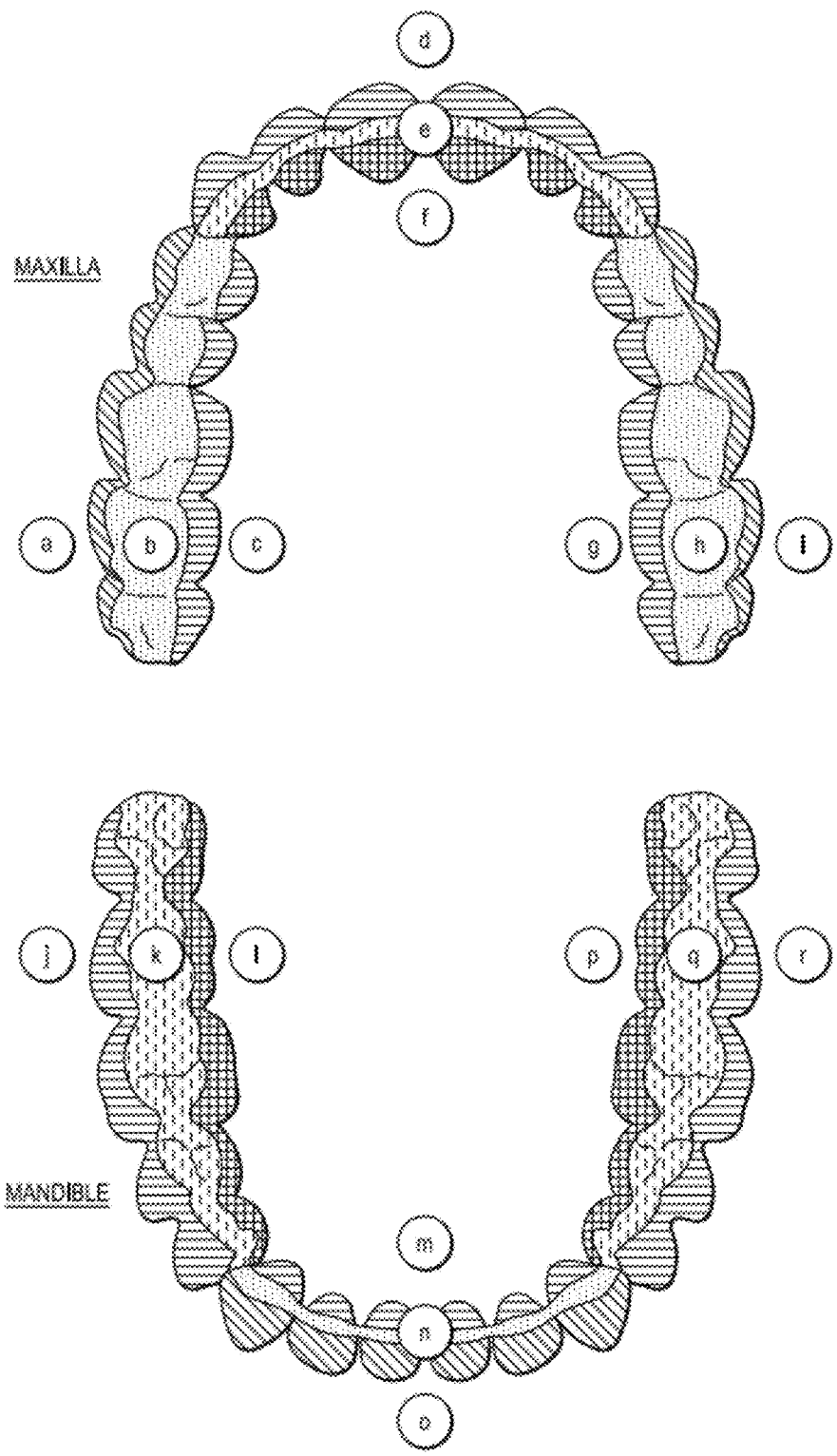
FIG. 8 is a diagram illustrating 18 tooth zones.

The oral cavity position of a toothbrush may be defined by the bristle side of the brushhead portion facing a tooth zone. The tooth zone means an area or a region on a tooth or teeth. The number and location of the tooth zone may vary based on a specific purpose. In one example, 18 tooth zones are divided around a user's teeth, as shown in FIG. 8. These 18 tooth zones are distinguished from each other by each one's unique location inside the oral cavity. These tooth zones include: cheek side of upper left back teeth (zone a), occlusal side of upper left back teeth (zone b), tongue side of upper left back teeth (zone c), front side of upper front teeth (zone d), occlusal side of upper front teeth (zone e), tongue side of upper front teeth (zone f), tongue side of upper right back teeth (zone g), occlusal side of upper right back teeth (zone h), cheek side of upper right back teeth (zone i), cheek side of lower left back teeth (zone j), occlusal side of lower left back teeth (zone k), tongue side of lower left back teeth (zone l), tongue side of lower front teeth (zone m), occlusal side of lower front teeth (zone n), front side of lower front teeth (zone o), tongue side of lower right back teeth (zone p), occlusal side of lower right back teeth (zone q), and cheek side of lower right back teeth (zone r).

In an embodiment, the oral cavity position of the brushhead portion is determined based on the contact information of each side of the brushhead portion with the cheek area, the tongue area or the saliva area. Table 1 shows an exemplary contact information of the first side 106, the rear side 104 and the second side 108 of the brushhead portion 10 as shown in FIGS. 2(a) and 2(b) when the bristle side 102 is facing each tooth zone.

TABLE 1

Exemplary contact information for each tooth zone

| Tooth zone faced by the bristle side 102 | Oral area contacted by the first side 106 | Oral area contacted by the rear side 104 | Oral area contacted by the second side 108 |
|---|---|---|---|
| a (cheek side of upper left back teeth) | cheek | cheek | saliva |
| b (occlusal side of upper left back teeth) | cheek | tongue | saliva |
| c (tongue side of upper left back teeth) | tongue | saliva | saliva |
| d (front side of upper front teeth) | No contact or saliva | No contact or saliva | No contact or saliva |
| e (occlusal side of upper front teeth) | No contact or saliva | No contact or saliva | No contact or saliva |
| f (tongue side of upper front teeth) | No contact or saliva | No contact or saliva | No contact or saliva |
| g (tongue side of upper right back teeth) | saliva | saliva | tongue |
| h (occlusal side of upper right back teeth) | saliva | tongue | cheek |
| i (cheek side of upper right back teeth) | saliva | cheek | cheek |
| j (cheek side of lower left back teeth) | saliva | cheek | cheek |
| k (occlusal side of lower left back teeth) | saliva | saliva | cheek |
| l (tongue side of lower left back teeth) | tongue | saliva | saliva |
| m (tongue side of lower front teeth) | No contact or saliva | No contact or saliva | No contact or saliva |
| n (occlusal side of lower front teeth) | No contact or saliva | No contact or saliva | No contact or saliva |
| o (front side of lower front teeth) | No contact or saliva | No contact or saliva | No contact or saliva |
| p (tongue side of lower right back teeth) | saliva | saliva | tongue |
| q (occlusal side of lower right back teeth) | cheek | saliva | saliva |
| r (cheek side of lower right back teeth) | cheek | cheek | saliva |

This exemplary contact information for each tooth zone is proved by 4 random testing users to have an average 90% accuracy during tooth brushing. The testing is done by asking the testing users to brush the 18 tooth zones in a specific order, recording the contact information for each tooth zone and then comparing the recorded contact information with the exemplary contact information as shown in Table 1. The accuracy and precision can be further improved by collecting more users' data to adjust the oral area to be contacted by each side of the brushhead portion during brushing. For example, some people may have their lips in contact with the first side 106 and the second side 108 of the brushhead portion 10 as shown in FIGS. 2(a) and 2(b) when the front side of upper front teeth and the front side of lower front teeth are brushed.

Based on the exemplary contact information as shown in Table 1, there are some tooth zones having same contact information, for example zone a and zone r, which therefore cannot be identified from each other based on the contact information only. Furthermore, zones d, e, f, m, n, and o cannot be identified from each other because there is no contact with the cheek or the tongue.

Figure 6:
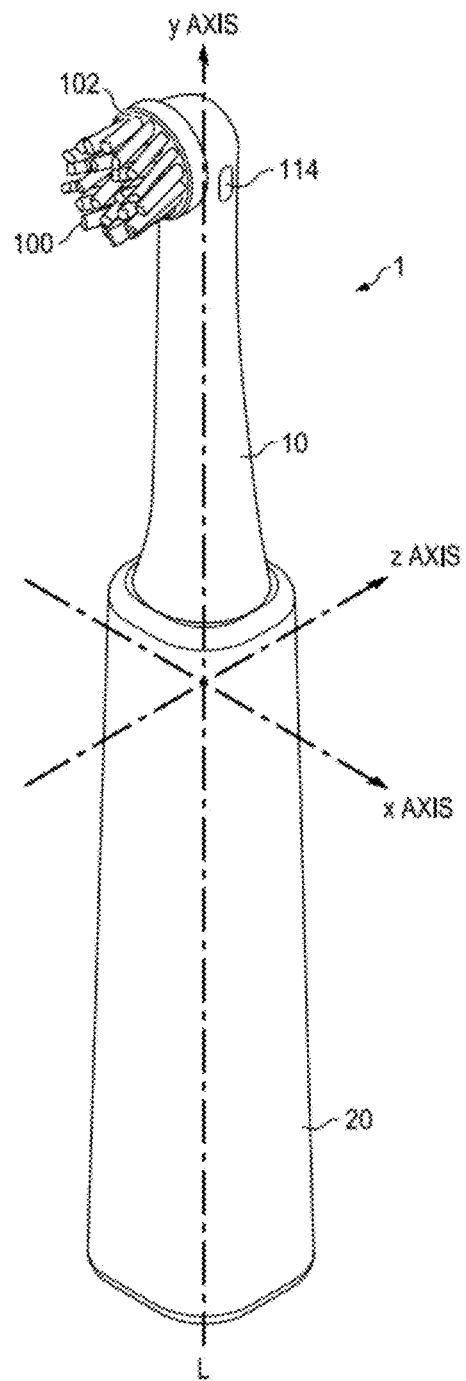
FIG. 6 illustrates an arrangement of x, y, and z axes of a 3-axis accelerometer installed within the toothbrush according to an embodiment of the present invention.

Therefore, in a further embodiment, the oral cavity position of the brushhead portion is determined by combining the contact information with orientation information of the toothbrush. The orientation information may comprise an orientation angle formed between the bristle side and a horizontal plane. With a 3-axis (x, y, and z axes) accelerometer installed within the toothbrush 1 as shown in FIG. 6, the x axis of the accelerometer is parallel to the bristle side 102 and orthogonal to a lengthwise elongation axis L of the toothbrush 1, so the angle formed between the x axis of the accelerometer and a horizontal plane may be taken as the orientation angle.

Figure 9:
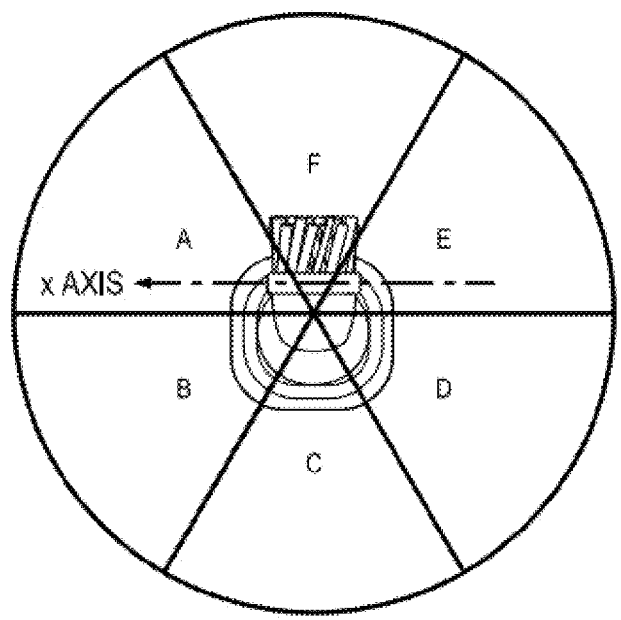
FIG. 9 is a diagram illustrating 8 orientation sectors of a toothbrush during brushing.
Figure 9:
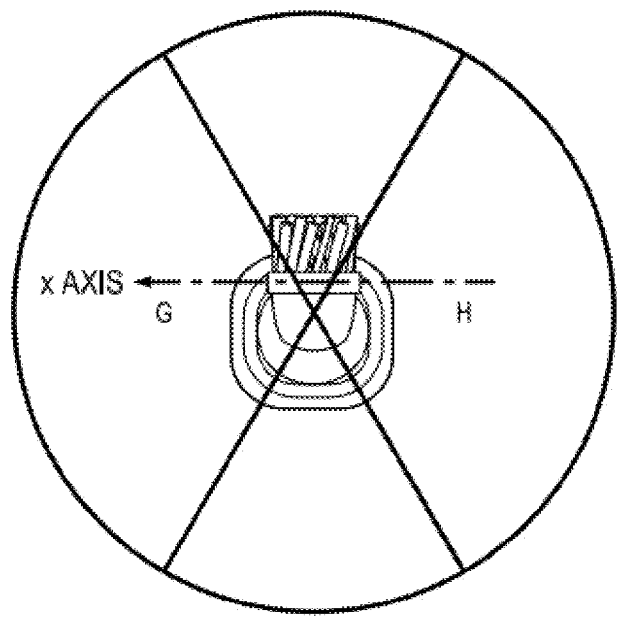

For convenience, the brush orientation, defined by the orientation angle, may be broken down into 8 orientation sectors A to H as shown in FIG. 9. Each of the sectors A to F is 60 degrees large. Sector G is a combination of sectors A and B. Sector H is a combination of sectors D and E. These 8 orientation sectors correspond to 8 typical brush orientations when the 18 tooth zones as shown in FIG. 8 are brushed during tooth brushing. For example, sector A corresponds to a brush orientation when the tongue side of upper left back teeth (zone c) is brushed, while sector B corresponds to a brush orientation when the tongue side of lower left back teeth (zone 1) is brushed. The orientation angle at sector A is about 60°. The orientation angle at sector B is about 120°. Table 2 shows the orientation angle of the toothbrush 1 and the tooth zone which might be brushed at each orientation sector.

TABLE 2

Orientation angle and tooth zone at each orientation sector

| Orientation sector | Orientation angle | Tooth zone which might be brushed |
|---|---|---|
| A | 60° | c (tongue side of upper left back teeth) |
| B | 120° | l (tongue side of lower left back teeth) |
| C | 180° | k (occlusal side of lower left back teeth) |
|   |   | m (tongue side of lower front teeth) |
|   |   | n (occlusal side of lower front teeth) |
|   |   | q (occlusal side of lower right back teeth) |
| D | 240° | p (tongue side of lower right back teeth) |
| E | 300° | g (tongue side of upper right back teeth) |
| F | 360° | b (occlusal side of upper left back teeth) |
|   |   | e (occlusal side of upper front teeth) |
|   |   | f (tongue side of upper front teeth) |
|   |   | h (occlusal side of upper right back teeth) |
| G | 90° | d (front side of upper front teeth) |
|   |   | i (cheek side of upper right back teeth) |
|   |   | o (front side of lower front teeth) |
|   |   | r (cheek side of lower right back teeth) |
| H | 270° | a (cheek side of upper left back teeth) |
|   |   | d (front side of upper front teeth) |
|   |   | j (cheek side of lower left back teeth) |
|   |   | o (front side of lower front teeth) |

Table 3 shows how each of the 18 tooth zones as shown in FIG. 8 is identified by the combination of the contact information and the orientation information. The previously brushed tooth zone is taken into consideration to identify the tooth zones relating to the front teeth where no contact information with the cheek or the tongue is obtained. This is based on an assumption that the user generally brushes teeth from one zone to another adjacent zone. An algorithm represented by table 3 may be programmed into the position determination unit 5000 (FIG. 5) to distinguish all 18 tooth zones from each other.

TABLE 3

Tooth zone identification by combining contact information and orientation information

| Tooth zone to be identified | Contact information | | | Orientation sector | Previously brushed tooth zone |
|---|---|---|---|---|---|
|   | Oral area contacted by the first side 106 | Oral area contacted by the rear side 104 | Oral area contacted by the second side 108 |   |   |
| a (cheek side of upper left back teeth) | cheek | cheek | saliva | H | — |
| b (occlusal side of upper left back teeth) | cheek | tongue | saliva | F | — |
| c (tongue side of upper left back teeth) | tongue | saliva | saliva | A | — |
| d (front side of upper front teeth) | No contact or saliva | No contact or saliva | No contact or saliva | G or H | a or i |
| e (occlusal side of upper front teeth) | No contact or saliva | No contact or saliva | No contact or saliva | F | b or h |
| f (tongue side of upper front teeth) | No contact or saliva | No contact or saliva | No contact or saliva | F | c or g |
| g (tongue side of upper right back teeth) | saliva | saliva | tongue | E | — |
| h (occlusal side of upper right back teeth) | saliva | tongue | cheek | F | — |
| i (cheek side of upper right back teeth) | saliva | cheek | cheek | G | — |
| j (cheek side of lower left back teeth) | saliva | cheek | cheek | H | — |
| k (occlusal side of lower left back teeth) | saliva | saliva | cheek | C | — |
| l (tongue side of lower left back teeth) | tongue | saliva | saliva | B | — |
| m (tongue side of lower front teeth) | No contact or saliva | No contact or saliva | No contact or saliva | C | l or p |

TABLE 3-continued

Tooth zone identification by combining contact information and orientation information

| Tooth zone to be identified | Contact information | | | Orientation sector | Previously brushed tooth zone |
|---|---|---|---|---|---|
| | Oral area contacted by the first side 106 | Oral area contacted by the rear side 104 | Oral area contacted by the second side 108 | | |
| n (occlusal side of lower front teeth) | No contact or saliva | No contact or saliva | No contact or saliva | C | k or q |
| o (front side of lower front teeth) | No contact or saliva | No contact or saliva | No contact or saliva | G or H | j or r |
| p (tongue side of lower right back teeth) | saliva | saliva | tongue | D | — |
| q (occlusal side of lower right back teeth) | cheek | saliva | saliva | C | — |
| r (cheek side of lower right back teeth) | cheek | cheek | saliva | G | — |

Therefore, all the 18 tooth zones are distinguished by the present invention in a non-intrusive, precise and accurate way at low cost. According to the present invention, the user doesn't have to wear any additional equipment which may be considered as being intrusive. Head movements and walking around while brushing do not disturb the position detection of the present invention as it is the case with the systems which use accelerometer only, so that good precision and accuracy are provided. The contact determination relies on electrode pairs which can be easily injected as a conductive paste in the toothbrush in mass production, which is favorably cost-effective.

In an even further embodiment, the oral cavity position of the brushhead portion is further determined by a tooth/gum brushing identification process. There is a temperature difference between tooth and gum. Temperature is higher in the gum where there is blood compared to tooth where there is no blood. Referring back to FIG. 5, a temperature is obtained by an infrared sensor 3100 during brushing. The temperature may be a bristle temperature or a temperature of an object facing the bristle side 102 of the brushhead portion 10 (see FIGS. 2(*a*) and 2(*b*)). If the temperature is greater than or equal to a first threshold (for example, 34.5° C.), it is determined that gum is being brushed. If the bristle temperature is less than the first threshold but greater than or equal to a second threshold (for example, 31° C.), it is determined that a tooth is being brushed. In the case that the infrared sensor may sense each bristle's temperature, a temperature map may be plotted for all the bristles so as to identify how many bristles are brushing teeth and how many bristles are brushing gum.

This tooth/gum brushing identification information is especially advantageous when the brushing time for each tooth zone is recorded as a feedback. By this brushing identification process, the gum brushing time and teeth brushing time may be separately recorded so that the user can get a more precise and more accurate brushing feedback.

User Interface

As shown in FIG. 5, the display 6000 and the indicator 7000 may be provided as a user interface, for displaying and indicating information associated with the oral cavity position, so that the user may improve the brushing quality by optimizing their brushing procedure based on this information.

In an embodiment, the display 6000 comprises a diagram illustrating 18 tooth zones as shown in FIG. 8. A real-time feedback may be provided by lightening the tooth zone which has been brushed or is being brushed during brushing. Another real-time feedback may be provided by showing green if the tooth zone has received enough brushing and showing red if not enough brushing. Additionally, the tooth zone may blink if there is too much brushing. A summary feedback may be provided by showing how much time is used for each tooth zone during and/or after the brushing. An overall brushing result may be provided by showing if any tooth zone was missed or if all the tooth zones have been brushed properly. Such feedback would motivate the user to re-brush the tooth zones which have been missed or not brushed with enough time. As an alternative embodiment, the toothbrush 1 may be able to wirelessly connect with a smart phone and use the screen of the smart phone as a display 6000.

In an embodiment, the indicator 7000 provides a visual, audio and/or physical signal to indicate the user to change the brushing tooth zone when the time used for one tooth zone is longer than a predetermined amount of time. The signals may be embodied on the toothbrush 1 or on the display 6000. For example, a physical signal may comprise the vibration of the toothbrush 1.

In an embodiment, the indicator 7000 provides a visual, audio and/or physical signal to indicate the user to deliver a specific active such as a whitening active on the tooth surface when a certain tooth zone is reached.

More information associated with the oral cavity position may be provided by a user interface to benefit the user, such as those disclosed in WO2008060482A2, paragraphs 24 to 26 of WO201177282A1, and columns 15 to 16 of U.S. Pat. No. 8,479,341B2. All the information may be displayed or indicated simultaneously or in sequence. The user may have a control on the information to be displayed or indicated.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method of detecting contact of a defined oral area selected from a cheek area, a tongue area, a saliva area, and combinations thereof by a side of an oral care implement comprising a brushhead portion of a toothbrush, the method comprising the steps:
    (a) providing an electrode pair on the side of the oral care implement;
    (b) electrifying the provided electrode pair with a voltage to form an impedance between the electrode pair;
    (c) applying at least two different frequencies to the voltage between the electrified electrode pair;
    (d) measuring impedance values of the formed impedance between the electrified electrode pair at the applied different frequencies, wherein the impedance values are selected from the group consisting of impedance magnitude, impedance phase, relative permittivity, and combinations thereof, and wherein the impedance values at the applied different frequencies are measured within a time interval of less than 50 ms;
    (e) defining a function that correlates impedance values of the defined oral area at the applied different frequencies;
    (f) processing the measured impedance values to the defined function so as to detect whether the side of the oral care implement is contacting the defined oral area, wherein the applied two different frequencies comprise a first frequency and a second frequency each of which is independently selected from 10 kHz to 100 kHz, the second frequency is greater than the first frequency, and the function comprises a formula:

$$\frac{A1}{A2} < a$$

wherein A1 is a first impedance magnitude measured at the first frequency, A2 is a second impedance magnitude measured at the second frequency, and α is a first threshold constant.

2. The method according to claim 1, wherein the defined oral area comprises the saliva area.

3. The method according to claim 1, wherein the defined oral area comprises a tongue area, and the function comprises a formula:

$$a \leq \frac{A1}{A2} < b$$

wherein b is a second threshold constant.

4. The method according to claim 1, wherein the defined oral area comprises a cheek area, and the function comprises a formula:

$$\frac{A1}{A2} \geq b$$

wherein b is a second threshold constant.

5. A method of determining an oral cavity position of an oral care implement, comprising the steps:
    (a) detecting contact information of the oral care implement by using the method according to claim 1, wherein the contact information comprises whether a side of the oral care implement is contacting a defined oral area;
    (b) detecting orientation information of the oral care implement; and
    (c) determining, based on at least the detected contact information and the detected orientation information, the oral cavity position of the oral care implement.

6. The method according to claim 5, wherein the brushhead portion comprises a bristle side with bristles disposed thereon for brushing teeth, and a rear side opposing the bristle side, and wherein the brushhead portion further comprises a first side, and a second side opposing the first side, wherein each of the first side and the second side separates the bristle side and the rear side, wherein the first side, the rear side, the second side, and the bristle side circumferentially define the brushhead portion, and wherein the contact information comprises information on whether one or more of the rear side, the first side, and the second side are contacting the defined oral area.

7. The method according to claim 6, wherein the orientation information comprises an orientation angle formed between the bristle side and a horizontal plane.

8. The method according to claim 7, wherein the oral cavity position is defined by the bristle side of the brushhead portion facing a tooth zone selected from the group consisting of a cheek side of upper left back teeth, an occlusal side of upper left back teeth, a tongue side of upper left back teeth, a front side of upper front teeth, an occlusal side of upper front teeth, a tongue side of upper front teeth, a cheek side of upper right back teeth, an occlusal side of upper right back teeth, a tongue side of upper right back teeth, a cheek side of lower left back teeth, an occlusal side of lower left back teeth, a tongue side of lower left back teeth, a front side of lower front teeth, an occlusal side of lower front teeth, a tongue side of lower front teeth, a cheek side of lower right back teeth, an occlusal side of lower right back teeth, a tongue side of lower right back teeth, and any combination thereof.

9. The method according to claim 1, wherein the first threshold a is from 1.2 to 1.4.

10. The method according to claim 4, wherein the second threshold b is from 1.7 to 2.1.

11. The method according to claim 3, wherein the first threshold a is from 1.2 to 1.4 and the second threshold b is from 1.7 to 2.1.

* * * * *